United States Patent [19]

Montaldi

[11] Patent Number: 5,018,507

[45] Date of Patent: May 28, 1991

[54] ONE-PIECE DISPOSABLE SPECULUM

[76] Inventor: David H. Montaldi, 2358 Howell Mill Rd., NW., Atlanta, Ga. 30318

[21] Appl. No.: 552,185

[22] Filed: Jul. 13, 1990

Related U.S. Application Data

[63] Continuation-in-part of Ser. No. 470,574, Jan. 26, 1990, Pat. No. 4,966,130.

[51] Int. Cl.$^5$ ............................................... A61B 1/30
[52] U.S. Cl. ..................................................... 128/17
[58] Field of Search .......................... 128/3, 17, 18, 20

[56] References Cited

U.S. PATENT DOCUMENTS

| | | | |
|---|---|---|---|
| 3,246,646 | 4/1966 | Murphy, Jr. | 128/17 |
| 3,841,318 | 10/1974 | Olson | 128/20 |
| 3,890,961 | 6/1975 | Moore et al. | 128/17 |
| 4,854,300 | 8/1989 | Corbo | 128/17 X |
| 4,966,130 | 10/1990 | Montaldi | 128/17 |

*Primary Examiner*—William H. Grieb
*Attorney, Agent, or Firm*—Cushman, Darby & Cushman

[57] ABSTRACT

A one-piece disposable speculum is provided having first and second blades which are interconnected at both the distal ends and proximal ends thereof. The bars which interconnect the distal ends of the blades are pivotally connected to each of the blades with a thinned portion of the material forming the blades and the bars so as to define a living hinge. The proximal ends of the speculum are adjustably interconnected with support bars provided on one blade which are selectively and adjustably connected with receiving elements provided on the other blade. The speculum can be moved from a compacted, insertion configuration to spaced apart, dilating configuration by moving one of the blade members relative to the other along the longitudinal axis of the speculum.

5 Claims, 2 Drawing Sheets

ONE-PIECE DISPOSABLE SPECULUM

This is a continuation-in-part of application Ser. No. 07/470,574 filed Jan. 26, 1990 now U.S Pat. No. 4,966,130, granted Oct. 30, 1990.

BACKGROUND OF THE INVENTION

1. Field of the Invention

The present invention relates to devices for dilating body orifices and, in particular, to a one-piece disposable speculum.

2. Description of the Related Art

Specula which are used for dilating body orifices to permit examination are well-known and are typically used for vaginal and anal examination. A typical speculum is shown, for example, in U.S. Pat. No. 3,246,646. That speculum has a pair of elongated members which are disposed in side-by-side relation and have confronting handles at a first end and confronting jaws at a second end thereof. The members are pivotally coupled together between the handles and the jaws so that movement of the handles towards one another spreads the jaws. The handles may be locked in a predetermined position to lock the speculum jaws in a spaced disposition. When the jaws are so locked, an opening is defined centrally through the speculum through which a visual examination can be made, a biopsy performed, secretory samples taken, etc.

Sterility of medical instruments has been a long standing concern in the medical field, as have costs of medical services and instruments. In an effort to minimize costs and eliminate the need for instrument sterilization by the medical practitioner, disposable specula have been proposed. An example of such a disposable speculum is disclosed in U.S. Pat. No. 3,890,961. Another example of a one-piece disposable speculum is shown in U.S. Pat. No. 3,841,318. However, the disposable specula which have been proposed to date suffer a number of deficiencies. For example, these specula fail to provide adequate adjustability of opening size to allow easy and versatile use of the specula. Thus, the more expensive metal instruments are generally preferred. Furthermore, existing disposable specula are often formed from two or three pieces which must be fitted together after manufacture and prior to use.

It would therefore be desireable to provide a one-piece disposable speculum which can be inexpensively produced for one-time use and which has a wide range of adjustability in use to enable quick and easy inspection of a particular body orifice.

SUMMARY OF THE INVENTION

The present invention provides a one-piece disposable speculum which overcomes the deficiencies of previously available disposable specula noted above. In particular, because the speculum provided in accordance with the present invention is of one-piece construction, no assembly of parts is required following manufacture and prior to use. Rather, a simple folding action places the speculum in its in use, insertion disposition. The speculum of the present invention further enables a wide variety of adjustments so that the varying requirements of the medical practitioner and the varying characteristics of the patient and orifices to be examined can be accommodated.

Thus, the disposable speculum provided in accordance with present invention includes a first blade member having a proximal end and a distal end and a second blade member having a proximal end and a distal end. The distal ends of the first and second blade members are interconnected by a first bar member and a second bar member, each of the first and second bar members being interconnected at each end thereof with the first and second blade members, respectively. The interconnection between each bar member and each blade member is defined by a thin portion of the material forming the bars and the respective blade member. Thus, a living hinge connection is provided whereby pivotal movement of the bar relative to each blade member can be accommodated.

A handle is defined at the proximal end of the first blade member. Further, one of the first and second blade members has an elongate adjustment or support element pivotally coupled to each longitudinal rear edge thereof. The other blade member includes an element for slidably receiving the support element whereby when the first blade member is disposed in parallel facing opposed relation to the second blade member so that the distal ends of the blade members are substantially adjacent to one another and the proximal ends of the blade members are disposed substantially adjacent to one another, the blades can be moved relative to one another so as to selectively dispose the blades in substantially immediately adjacent disposition, or spaced apart from one another a distance defined at the distal end by the connecting bar members and at the proximal end by a position of the support elements relative to the receiving elements. By adjusting the disposition of the support bars relative to the receiving elements, the spaced apart relation of the proximal ends of the blade members can be adjusted so as to vary the dilation effected by the speculum and facilitate examination and sampling by the medical practitioner.

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures.

DETAILED DESCRIPTION OF THE PREFERRED EMBODIMENT

Figure 1:
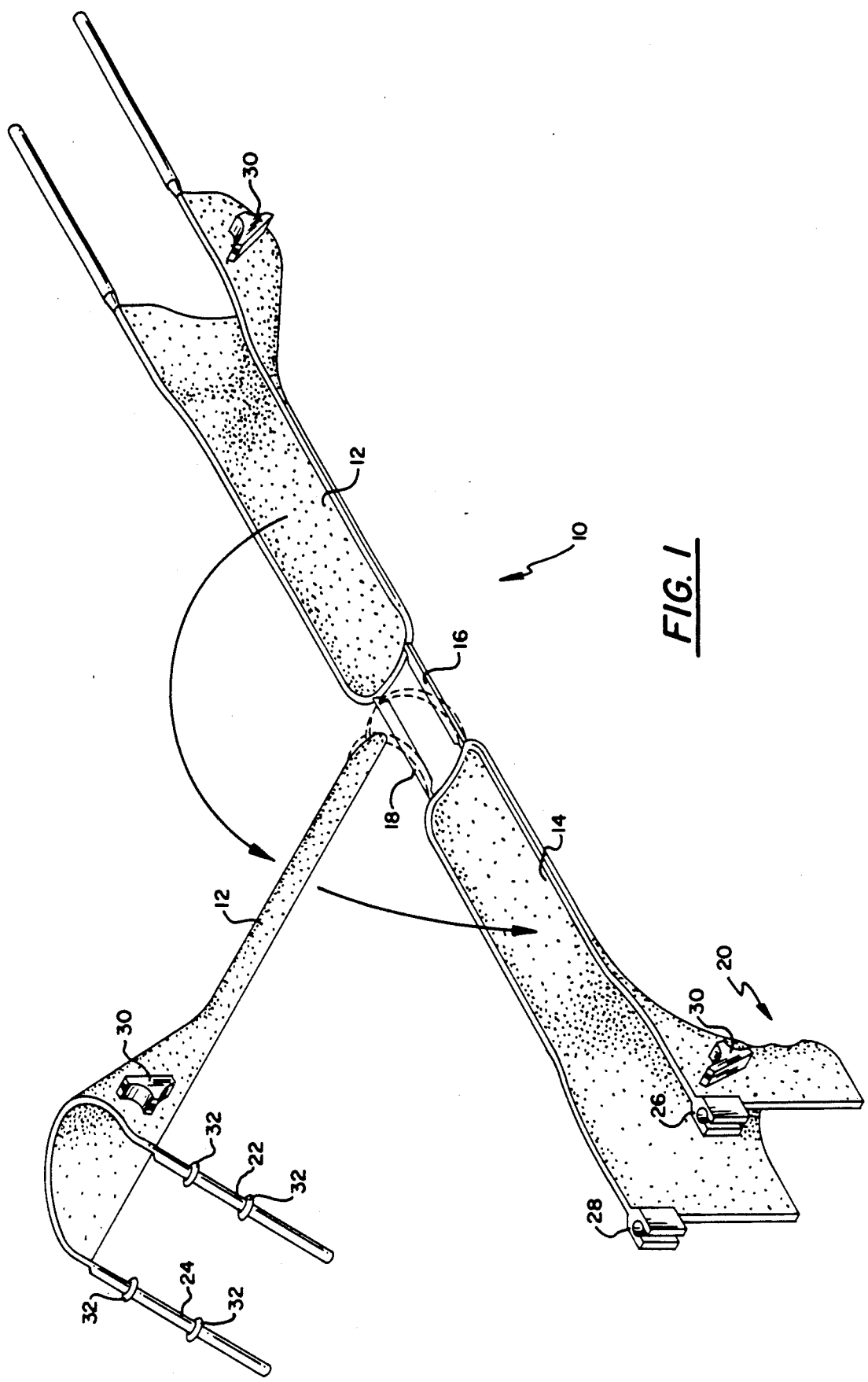
FIG. 1 is an isometric view of a one-piece disposable speculum provided in accordance with the invention.

A one-piece disposable speculum 10 formed in accordance with the present invention can be molded as a unitary structure to define first and second blade members 12, 14 which are interconnected by first and second bar members 16, 18. One of the blade members 14 has a handle 20 molded to the proximal end thereof. Furthermore, support structures are molded to the blades adjacent a proximal end thereof as discussed more fully below.

The bars 16, 18 which extend between and connect the blade members are pivotally connected at each end thereof to each of the blade members 12, 14. This pivotal coupling is preferably a thinned portion of the plastic material from which the disposable speculum is formed which allows the unitary construction to fold at the junction of each bar and each speculum blade. Such a thinned, pivotal connection is known as a living hinge.

First and second support or adjustment bars 22, 24 are pivotally connected to the upper blade 12 member at its proximal end. In the illustrated embodiment, the pivotal connections between the support bars 22, 24 and the upper blade member 12 are again provided by a thinned portion of the plastic which forms the speculum 10 and thus a living hinge is preferably defined between each of the support bars 22, 24 and the upper blade member 12. Each living hinge is preferably defined so that the support bars are pivotal in planes parallel to the longitudinal axis of the speculum, as shown. Although not illustrated in particular, the support bars can be connected to the lower blade and extend toward the upper blade without departing from this invention.

Figure 3:
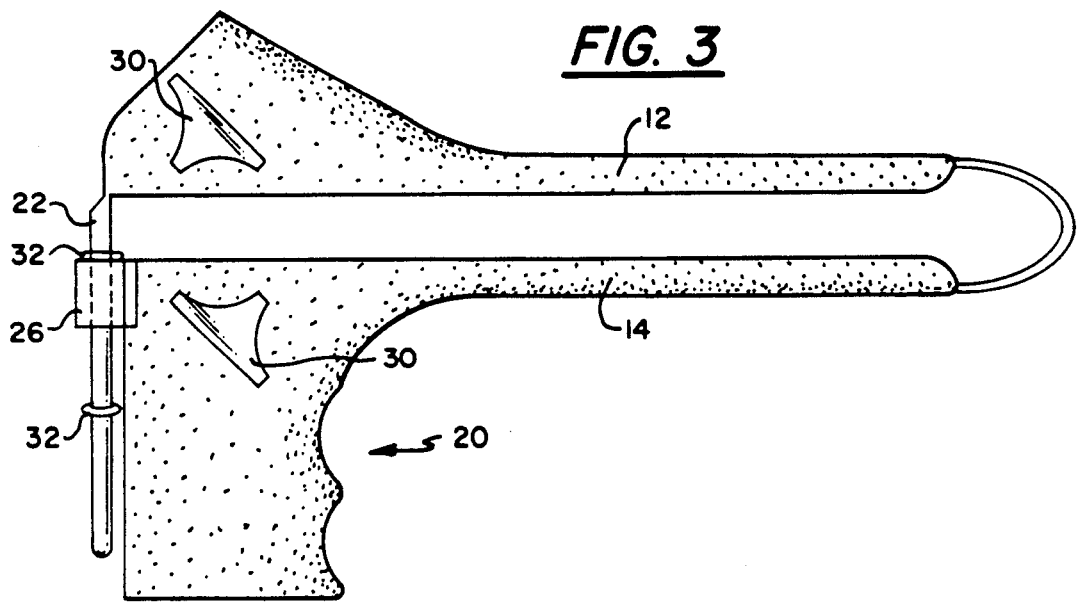
FIG. 3 is a side elevational view showing the speculum of the invention in its in use position.

Prior to insertion of the speculum 10 into a selected body orifice, the speculum 10 is folded from the disposition as shown in FIG. 1 to the in use configuration shown in FIG. 3 which facilitates insertion into the body orifice. As can be seen, when folded the blade members 12, 14 of the speculum are disposed in substantially opposed facing relation and may be longitudinally offset from one another with the bar members pivoted with respect to the distal end of each of the blades so as to minimize the vertical height of the device. The support bars at the proximal ends of the upper blade are pivoted relative to the upper blade and engaged with the receiving elements 26, 28 provided on the lower blade 14 to define the diameter of the speculum at its proximal end. Although not necessary, the support bars and receiving elements can be disengaged during insertion and engaged thereafter as will become more apparent below.

Once the speculum has been folded to its in use position (FIG. 3), handle 20 is grasped by the practitioner and used to push the speculum forward towards and into the body cavity so as to fully insert the speculum 10. Once the speculum has been inserted into the body orifice to be dilated and examined and in order to examine the interior of the body orifice, the upper blade 12 is pushed along its longitudinal axis relative to the lower blade 14. Specifically, the thumb or the other hand may be used to push the proximal end of the upper blade and in particular the projections 30 to displace the speculum blade and dilate the body cavity. Because the distal ends of the speculum blades are interconnected by bars 16, 18 and the proximal ends are interconnected by support bars 22, 24 and receiving elements 26, 28, longitudinal movement of the upper blade 12 will pivot the upper blade 12 to displace the same vertically from the lower blade 14. The vertical displacement of the upper blade 12 relative to the lower blade 14 simultaneously dilates the body orifice into which the speculum was inserted. Once the speculum is inserted, the size of the opening can be adjusted by separating the blades from one another and maintaining the blades in that spaced disposition by interconnecting the support bars 22, 24 with the receiving elements 26, 28. Beaded portions or flanges 32 can be defined at spaced locations along the length of each support bar so as to define particular spacings of the proximal ends of the blades.

As is further apparent from the foregoing, the spacing of the distal ends of the blade can be varied by altering the longitudinal position of the upper blade with respect to the lower blade. The maximum distal dilation of the distal end is effected when the upper and lower blades are inserted to the same depth. Furthermore, the proximal end of the speculum can be varied in vertical disposition to obtain a desired proximal dilation. The support bars maintain that dilation.

Figure 2:
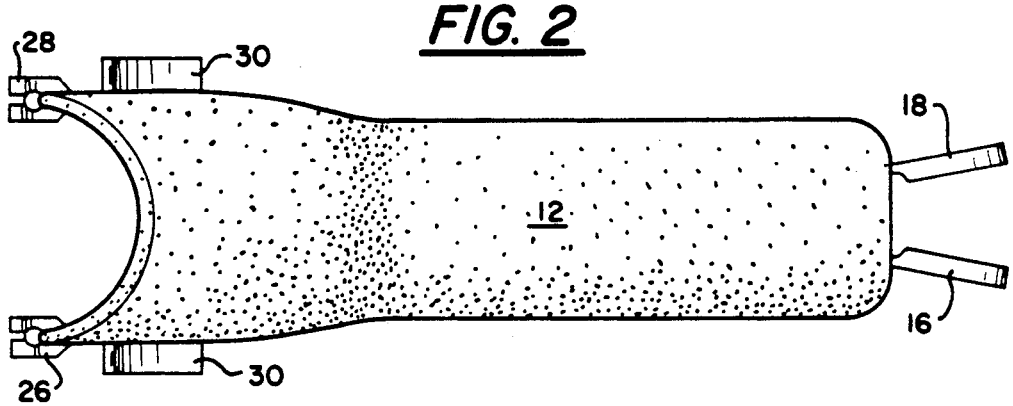
FIG. 2 is a top plan view of a one-piece disposable speculum provided in accordance with the present invention.
Figure 4:
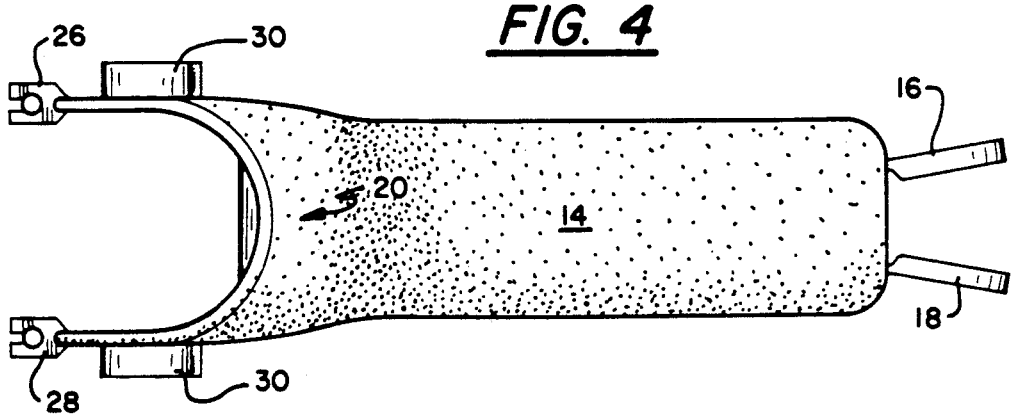
FIG. 4 is a bottom plan view of the speculum shown in FIG. 3.

Typically, in use, there will be a certain amount of compression force from the orifice acting on the speculum blades. This will tend to force the blades towards one another from a fully vertically spaced disposition. In response to these compression forces, a slight forward and lateral bowing may be seen in the bars 16, 18 at the distal end of the speculum (FIGS. 2-4) and/or in the support bars 22, 24. This bowing causes the bars 16, 18 to take on a ring-like appearance but which will generally not interfere with the use of the device nor the dilation effected thereby.

As can be further seen, in particular in FIGS. 1 and 3, each of the blades of the speculum provided in accordance with the present invention is substantially rounded in cross-section. The rounded configuration substantially corresponds to the round shaped orifices with which the speculum is used and thus increases the comfort for the patient and enables uniform dilation of the body passage.

As is apparent from the foregoing, the speculum of the invention can be injection molded or otherwise formed from a resilient plastic material. As the speculum is most preferably used for medical purposes, the plastic should be biocompatible.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed is:
1. A disposable speculum comprising:
a first blade member having a proximal end and a distal end;
a second blade member having a proximal end and a distal end, the distal ends of the first and second blade members being interconnected by first and second substantially parallel, spaced apart bar members, each of said bar members being formed integrally with said first and second blade members so as to be interconnected at each end thereof with a respective blade member, the interconnection between each end of each bar member and each said blade member being defined by a thinned portion of the material forming the bar member and the blade member so as to provide a living hinge connection;
a handle defined at said proximal end of said first blade member;
one of said blade members having an elongate support bar pivotally coupled to each longitudinal rear edge thereof;
the other blade member including means for slidably receiving said support bars, whereby when said first blade member is disposed in parallel facing opposed relation to said second blade member so that the distal ends of said blade members are substantially adjacent to one another and the proximal ends of the blade members are disposed substantially adjacent to one another, the blades can be moved longitudinally relative to one another so as to selectively dispose the blades in immediately adjacent disposition or spaced apart from one another a distance defined at the distal end by the bar members and at the proximal end by a position of the support bars relative to said receiving means.

2. A speculum as in claim 1, wherein at least said first and second blade members are formed from a biocompatible plastic material.

3. A speculum as in claim 1, wherein a plurality of flange elements are defined at spaced locations along the length of each of said support bars so as to define a plurality of positions of said support bars relative to said receiving elements so that a spacing between said first blade member and said second blade member at said proximal ends thereof can be varied.

4. A speculum as in claim 1, wherein said support bars are interconnected to said longitudinal rear edge of said one blade member with a thinned portion of the material forming the support bars and the one blade so as to define a living hinge.

5. A speculum as in claim 1, wherein each said blade member has a rounded cross-section.

* * * * *